US010154828B2

(12) United States Patent
Buchalter

(10) Patent No.: US 10,154,828 B2
(45) Date of Patent: Dec. 18, 2018

(54) PROTECTIVE COVER SET FOR A MEDICAL PROBE

(71) Applicant: Parker Laboratories, Inc., Fairfield, NJ (US)

(72) Inventor: Neal Buchalter, Short Hills, NJ (US)

(73) Assignee: Parker Laboratories, Inc., Fairfield, NJ (US)

( * ) Notice: Subject to any disclaimer, the term of this patent is extended or adjusted under 35 U.S.C. 154(b) by 197 days.

(21) Appl. No.: 15/082,861

(22) Filed: Mar. 28, 2016

(65) Prior Publication Data

US 2016/0278738 A1  Sep. 29, 2016

Related U.S. Application Data

(60) Provisional application No. 62/139,144, filed on Mar. 27, 2015.

(51) Int. Cl.
*A61B 1/00* (2006.01)
*A61B 8/00* (2006.01)
*B32B 1/08* (2006.01)
*B32B 1/02* (2006.01)
*A61B 8/12* (2006.01)

(52) U.S. Cl.
CPC ........ *A61B 8/4422* (2013.01); *A61B 1/00142* (2013.01); *A61B 1/00144* (2013.01); *A61B 8/12* (2013.01); *A61B 8/42* (2013.01); *B32B 1/02* (2013.01); *B32B 1/08* (2013.01)

(58) Field of Classification Search
CPC ... A61B 1/00142; A61B 1/00144; A61B 8/12; A61B 8/42; A61B 8/4422; B32B 1/02; B32B 1/08
See application file for complete search history.

(56) References Cited

U.S. PATENT DOCUMENTS

| 4,408,692 A | 10/1983 | Arkans et al. |
| 4,593,699 A | 6/1986 | Poncy et al. |
| 5,069,337 A * | 12/1991 | Bala ................. G01K 1/083 206/212 |
| 5,676,159 A | 10/1997 | Navis |
| 5,795,632 A | 8/1998 | Buchalter et al. |
| 6,402,695 B1 | 6/2002 | Grimm et al. |
| 7,665,893 B2 | 2/2010 | Buchalter et al. |

FOREIGN PATENT DOCUMENTS

WO  0039003  6/2000

OTHER PUBLICATIONS

EP16162619.7, "Extended European search report", dated Aug. 23, 2016, 6 pages.
EP16162619.7, "Communication pursuant to Article 94(3) EPC", dated Feb. 27, 2018, 4 pages.

* cited by examiner

*Primary Examiner* — Walter Aughenbaugh
(74) *Attorney, Agent, or Firm* — Kilpatrick Townsend & Stockton LLP

(57) ABSTRACT

Embodiments of a protective cover set for a medical probe are described herein, which may include an elongate protective cover having two or more fastening elements, with at least one fastening element at a point along the length of the protective cover. Embodiments may be configured to fit within a removable outer wrapper.

17 Claims, 3 Drawing Sheets

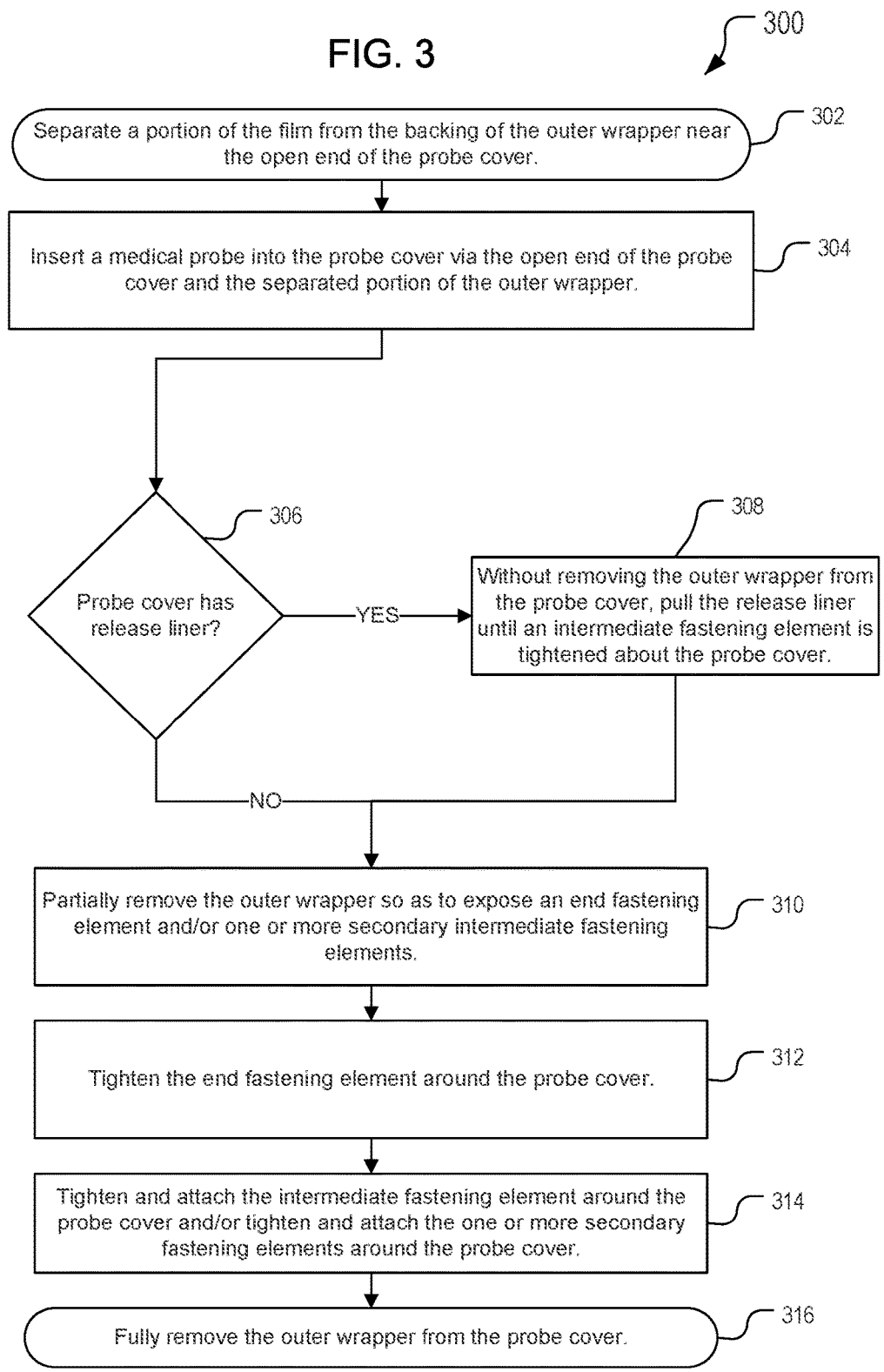

PROTECTIVE COVER SET FOR A MEDICAL PROBE

CROSS-REFERENCES TO RELATED APPLICATIONS

This application claims the benefit of U.S. Provisional Application No. 62/139,144, filed Mar. 27, 2015, the entire disclosure of which is hereby incorporated herein by reference.

BACKGROUND

A variety of medical applications require the use of non-disposable devices, such as medical probes, scopes, and cameras, which may be difficult to fully sterilize, or which may malfunction, if exposed directly to bodily tissues or fluids. One such device is an ultrasound device, which tends also to possess a physical connection by way of a wire, cable, or flexible tube to a base station which processes a signal delivered along the wire. Many other electronic instruments in such fields as medicine, veterinary medicine, and dentistry possess similar connections.

Existing methods of protecting such instruments from contamination with bodily fluids include the use of protective covers, such as those described in U.S. Pat. No. 7,665,893, and U.S. Pat. No. 5,795,632. These above-cited references have been assigned to the same assignee and are incorporated by reference in their entirety. However, such protective covers provide limited protection to the device and patient when the device possesses a cord.

BRIEF SUMMARY

Embodiments disclosed herein relate to, for example, a protective cover set which may include an elongate probe cover, which may also have a removable outer wrapper. Embodiments of the protective cover may have a fastening element attached at or near one or more mid-points along the length of the cover, and such fastening elements may be enclosed within an outer wrapper when the outer wrapper is enveloping the probe cover. Embodiments may also possess a fastening element proximate to an open end of the probe cover.

BRIEF DESCRIPTION OF THE DRAWINGS

Various embodiments in accordance with the present disclosure will be described with reference to the drawings, in which:

FIG. 3 illustrates a process for using a protective cover set with a medical probe.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments herein disclosed relate to a protective cover set for a medical probe for various medical applications such as interoperative use within an incision in a human or animal body, or for insertion into an endocavity. Embodiments may possess any or all of an elongate probe cover, one or more fastening elements, and an outer wrapper. For purposes of this application, the term "probe" may be used to mean any suitable medical device including but not limited to a scope, camera, or other medical device for insertion into an endocavity or incision; and the term "probe cover" may be used to refer to a cover for any of the above referenced medical tools.

Figure 1:
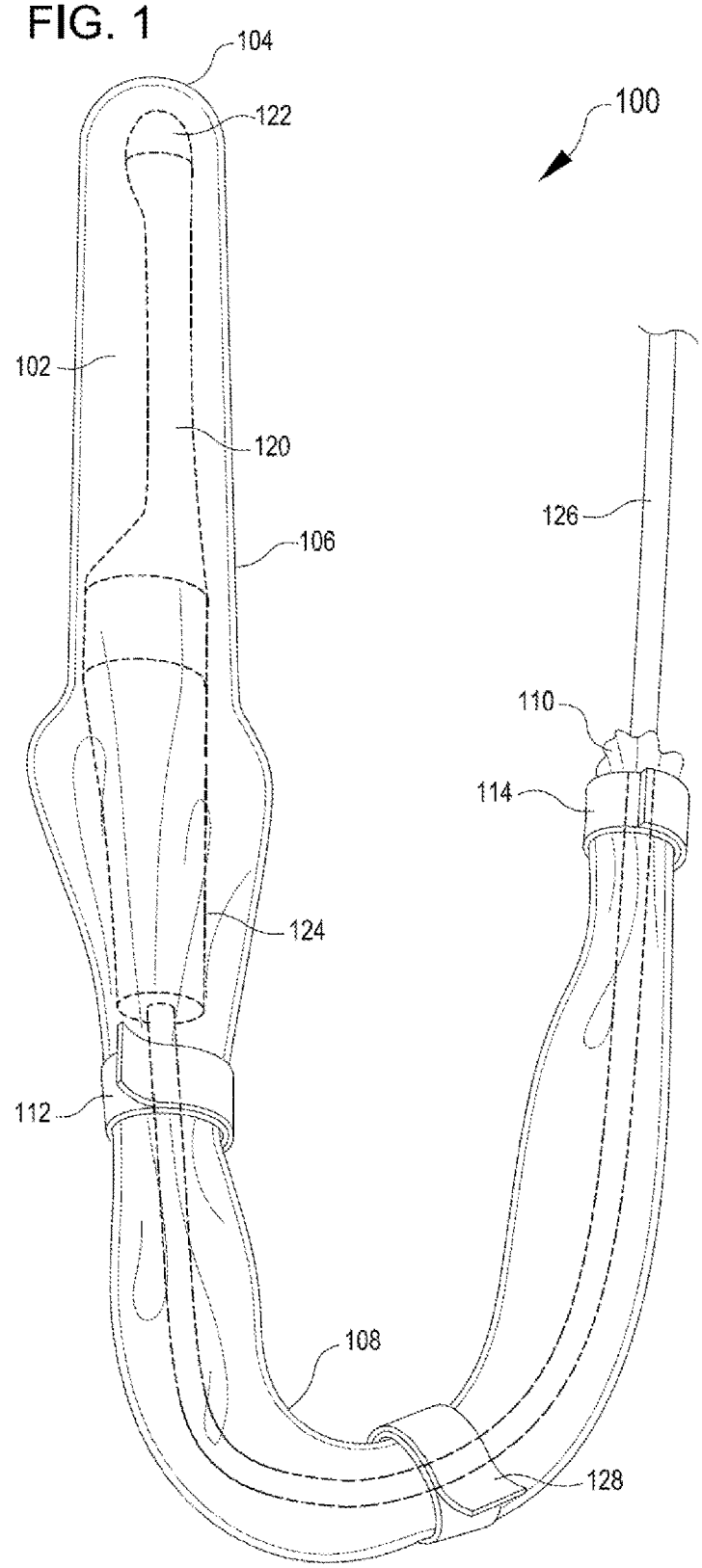
FIG. 1 shows a probe cover attached with a medical device, in accordance with embodiments.

FIG. 1 shows an example of an assembly 100 of a probe cover 102 attached with a medical probe 120, in accordance with embodiments. The probe cover 102 has a closed end 104, a first section 106 that is proximal to the closed end, a second section 108 distal from the closed end, and an open end 110 distal of the second section. In this example, a medical probe 120 is inserted into the probe cover 102 such that a working end 122 of the medical probe abuts an interior wall of the closed end 104 of the probe cover, and such that a handle 124 of the medical probe is fully enclosed in the first section 106 of the probe cover. The first section 106 of the probe cover is bounded by the closed end 104 at one end and by an intermediate fastening element 112, such that the fastening element can secure the probe cover beyond the handle 124 of the medical probe 120; and the second section 108 of the probe cover 102 encloses a portion of cord 126 attached with the medical probe.

The second section 108 is bounded at one end by the intermediate fastening element 112 and at the other end by the open end 110 of the probe cover. An end fastening element 114 may be present at or near the open end 110 of the probe cover to secure the open end of the probe cover 102 to the medical device cord 126. In some embodiments, one or more secondary intermediate fastening elements may be present (e.g., secondary intermediate fastening element 128) along a length of the second section 108. Secondary intermediate fastening elements may be used for securing the probe cover 102 around the medical probe 120, particularly along the cord 126 of the medical probe.

In some embodiments, the probe cover 102 is an elongate sheathe of one or more biocompatible polymers having a closed end and an open end. The biocompatible polymer(s) may be any suitable material which can be configured to minimize irritation to an endocavity or incision, in accordance with embodiments. The biocompatible polymer(s) may be configured to prevent contamination of a probe with biological material. In some cases, the probe cover 102 may be nonporous, so as to prevent transfer of biological material to the medical probe 120. In some cases, the probe cover 102 may be sterile, so as to prevent transfer of contaminants from the probe cover 102 to a patient.

A biocompatible material for the probe cover 102 may include any suitable flexible polymer, and in particular may be a non-irritating and non-sensitizing material, in accordance with embodiments. Particular materials which may be used include urethane and polyethylene, but the probe cover may be any suitable material having properties of flexibility, at least partial transparency, and biocompatibility, that is capable of forming a membrane that is impermeable to biological material. Embodiments of the probe cover 102 may be formed of any one or any combination of: thermoplastic polyurethane (TPU), thermoplastic polyethylene (TPE), polyethylene, any suitable alternative material, or blends of suitable materials.

In some embodiments, the probe cover may be a combination of two or more materials. For example, some embodiments may be formed by heat-sealing two polymer layers together at edges of the layers; and the two polymer layers may be the same polymer or may be different. In one such embodiment, the lower layer may be urethane, for providing structure and a soft surface, while the top layer may be polyethylene for improved transparency, among other characteristics. The materials forming the bottom and top layers may be any other suitable materials having similar characteristics, the materials may be reversed, or both layers may be formed of the same material.

In alternative embodiments, one or both of the upper and lower layers of the probe cover may be a transparent urethane or urethane blend.

The probe cover may be significantly elongate in accordance with embodiments, for applications such as preserving the sterility of an operating environment by covering a probe or medical device that has a connection to equipment beyond the immediate operating zone. Embodiments that are significantly elongate may have a flattened width ranging from approximately ¼ to 4 inches; but have a length up to or exceeding approximately 10 inches, 14 inches, 24 inches, or greater. The dimensions of specific embodiments may vary significantly depending on the particular use.

Various embodiments of a protective cover set may possess fastening elements attached with the probe cover. A fastening element may be, for example, an adhesive strip fixedly attached at one end to a backing strip, with the backing strip being fixedly attached to a point on the probe cover. The fastening element may be used by peeling the adhesive strip portion upward away from the backing, crimping or folding a portion of the probe cover toward the upraised adhesive strip, and then wrapping the adhesive strip around the probe cover to secure the crimped or folded portion. In some embodiments, the adhesive strip may be applied directly to a part of the medical probe, for example, an adhesive strip at the open end of the probe cover may wrap around the cord of the medical probe and attach either directly to the cord, attach to itself, or both.

In some embodiments, a fastening element may be any suitable non-adhesive fastener. Exemplary non-adhesive fasteners include, but are not limited to: hook-and-loop closures (e.g., Velcro® fasteners or similar), locking plastic ties, or one or more pliable wire ties that may be secured around the probe cover. A protective cover set may use also fastening elements comprising both some adhesive fasteners and some non-adhesive fasteners. For example, some fastening elements may be adhesive fasteners while other fastening elements may be non-adhesive fasteners in the same probe cover set. In a particular embodiment, an intermediate fastening element is an adhesive strip, while a secondary intermediate fastening element and an end fastening element are non-adhesive fasteners.

Various embodiments of a protective cover set may also possess an outer wrapper. The outer wrapper may be formed of a backing and a film, where the backing may selected for strength from any suitable material, for example Nylon polyester, polyethylene terephthalate (PET), or any polymer reinforced with one of the above, or with any suitable reinforcing material. Some embodiments of the probe cover may be significantly elongate, such that the outer wrapper is also significantly elongate, and may possess structural characteristics provided by inclusion of a high-strength polymer as the backing layer, a high-strength bottom layer in the backing, or strips of a high-strength material in one or both of the backing and film, to enhance usability by preventing tearing or breaking of the probe cover during application of the probe cover to a medical probe.

Figure 2:
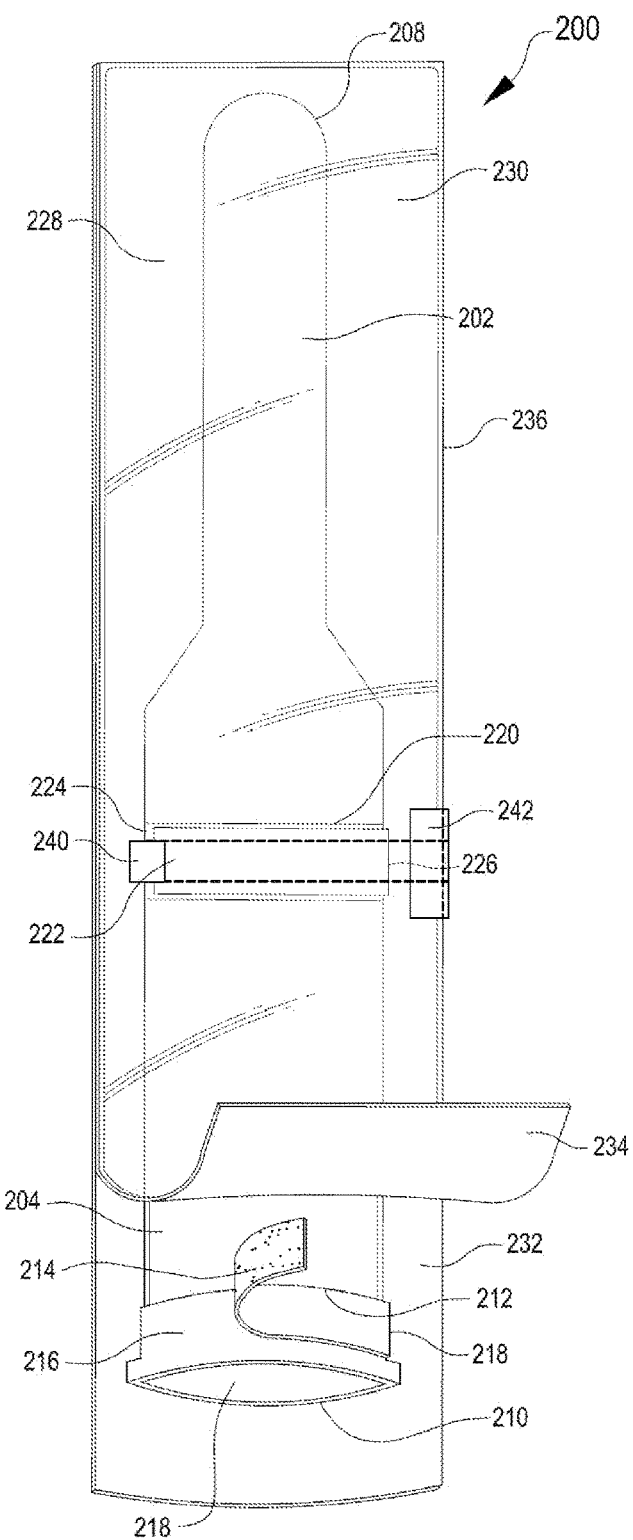
FIG. 2 shows an embodiment of a probe cover assembled with an outer wrapper.

FIG. 2 shows an example of a protective cover set 200 including a probe cover 202 enclosed in an outer wrapper 230, in accordance with embodiments. The probe cover 202 is formed of two flat layers of biocompatible polymer bonded together, a front layer 204 and a back layer 206, which may be heat bonded at their respective perimeters, in accordance with embodiments. The probe cover has a closed end 208 and an open end 210, and has an end fastening element 212 attached with a superior surface of the front layer.

In various embodiments, the end fastening element 212 is formed of an adhesive strip 214 and a backing layer 216, with the adhesive strip and backing layer being connected along a contiguous seam 218 at an end of the adhesive strip. The backing layer 216 is fixedly attached with the front layer 204.

In embodiments, the probe cover 202 also includes an intermediate fastening element 220, which may be formed of an intermediate adhesive strip 222 and an intermediate backing layer 224 attached with one another at an intermediate contiguous seam 226. The intermediate fastening element 220 is attached with the superior face of the front layer 204 of the probe cover by attachment of the intermediate backing layer 224 to the front layer 204 at a point between the closed end 208 and open end 210 of the probe cover. In some embodiments, the intermediate fastening element 220 is attached at a midpoint between the closed end 208 and open end 210.

The protective cover set 200 also includes an outer wrapper 230 in accordance with embodiments. The outer wrapper 230 has a backing 232 and a removable film 234, with the backing and removable film being loosely attached about a perimeter seam 236 of the wrapper such that the film can be separated from the backing by hand.

In some embodiments, one or both of the removable film 234 and backing 232 may terminate short of the open end 210 of the probe cover, such that the end fastening element 212 may be accessible to a user prior to separating the film from the backing. In such embodiments, the end fastening element may be secured about a portion of an inserted medical probe prior to removing the outer wrapper 230. In alternative embodiments, the backing may terminate at the same point as the probe cover, but the film may terminate short of that point.

In some embodiments, the intermediate fastening element 220 may possess features for securing the intermediate adhesive strip 222 about the probe cover 202 without having to remove the outer wrapper 230. For example, a protective cover set 200 can include a release liner 240 connected with the intermediate adhesive strip 222. The release liner 240 can extend around the probe cover 202 so that, when pulled, it can tighten the intermediate adhesive strip 222 around the probe cover. The release liner 240 can extend outside of the outer wrapper 230 and may include features for facilitating manual release, e.g., a pull tab 242. In such cases, a user can manually release the release liner 240, e.g., by pulling the pull tab 242. By way of further example, the release liner may be an extension of the intermediate adhesive strip 222 passing underneath the back layer 206 of the probe cover, and passing through an edge of the outer wrapper 230 such that it can be pulled by a user, securing the intermediate adhesive strip around a portion of the probe cover.

In an alternative embodiment of the probe cover set 200, the top layer of the probe cover may be slightly shorter than the bottom layer of the probe cover, and a double-sided adhesive and release liner may be adhered to the bottom layer. The release liner is accessible to a practitioner after the probe is inserted into the probe cover, but before the cover is removed. The practitioner may remove the release liner and adhere the bottom layer of the cover to the inserted probe and to a portion of the top layer of the probe cover before removing the outer wrapper from the assembled probe and probe cover.

In some embodiments, the space 228 between the probe cover 202 and the outer wrapper 230 contains a gel, such as an ultrasound gel, a medical lubricant, or other gel. In some additional embodiments, an interior space within the probe cover contains a gel, such as a gel for conducting ultrasound. The gel can be prepackaged inside the probe cover 202, including when the probe cover is packaged within an outer wrapper 230. The gel is preferably located close to the closed end of the probe cover 202 so that, when a medical probe (e.g., an ultrasound transducer) is fully inserted into the probe cover, the working end of the medical probe contacts the gel. The gel being prepackaged in the cover can eliminate a cumbersome step of an end user attempting to insert gel into a closed end of a cover.

In some embodiments, the space 228 between the probe cover 202 and the outer wrapper 230 is a sterile environment, so that the outer surfaces of the probe cover will be substantially sterile and separated from the environment until the film 324 is peeled from the wrapper backing 232.

Some alternative embodiments may also include a secondary wrapper for storing or maintaining the sterility of one or more of the probe cover sets. For example, each probe cover set, comprising a probe cover in an outer wrapper, may be additionally contained within a secondary wrapper, and the environment within the secondary wrapper may be sterile, such that the probe cover set including the outer wrapper is sterile at a time when it is removed from the secondary wrapper. The secondary wrapper may be formed, for example, of a high strength water-impermeable material such as TYVEK™, nylon, a fiber-reinforced polymer, or other suitable material. More than one probe cover set may be included in a secondary wrapper.

In some embodiments, the backing 232 and film 234 may be different materials. For example, the backing 232 may be a polymer or treated paper material having relatively high strength but lacking transparency, while the film 243 may be relatively thin, transparent, and low-strength compared to the backing. In embodiments including a significantly elongate probe cover, a high-strength wrapper backing may significantly improve usability by allowing a user to tear off the backing in a single continuous motion.

Various embodiments may possess alternative configurations of the probe cover and adhesive strips, including multiple intermediate adhesive strips. In some embodiments, an intermediate adhesive strip may be located at a midpoint of the probe cover; but in other embodiments, a first intermediate adhesive strip may be located at a point determined relative to a length of a medical probe. For example, supposing a common medical probe has a length of approximately 4 inches and the probe cover is approximately 24 inches long, multiple intermediate adhesive strips may be located at approximately 5 inches (for securing the probe) and again at an intermediate point (12 inches) in addition to the end fastening element at the open end (24 inches).

FIG. 3 illustrates a process 300 for using a protective cover set with a medical probe. Aspects of the process 300 may be performed, in some embodiments, with a probe cover and medical probe similar to those shown FIG. 1 (probe 120 and probe cover 102), and/or with a probe cover and outer wrapper similar to the probe cover 202 and outer wrapper 230 shown in FIG. 3.

In an embodiment, the process 300 includes separating a portion of a film from a backing of an outer wrapper (act 302). The separated portion is near an open end of a probe cover contained within the outer wrapper, so as to expose the open end of the probe cover. Next, the process includes inserting a medical probe, e.g., an ultrasound probe, into the open end of the probe cover within the outer wrapper (act 304). The medical probe can be fully inserted into the probe cover so that a working end of the medical probe is close to or in contact with a closed end of the probe cover. In embodiments having a gel within the probe cover, the medical probe can be fully inserted until the working end of the medical probe is in contact with the gel near or abutting the closed end of the probe cover. In some embodiments, the probe cover may have a release liner accessible to a user outside of the outer wrapper (306). The release liner can be pulled around a portion of the medical probe from outside the wrapper, entraining an intermediate adhesive strip to tighten and/or attach the intermediate adhesive strip around the probe cover and contained probe (act 308). Next, the outer wrapper can be partially removed to expose an end fastening element (act 310). In some cases, the outer wrapper may be removed to expose additional, secondary intermediate adhesive strips, similar to the secondary intermediate adhesive strip 128 (FIG. 1). The end fastening element can be tightened and attached around the probe cover containing the probe (act 312), and any exposed intermediate fastening element or secondary intermediate fastening elements may also be tightened and attached around the probe cover (act 314). Finally, the outer wrapper may be fully removed from the probe cover prior to use (act 316). The staged removal of the outer wrapper (e.g., separating 302, partially removing 310, and fully removing 316) can facilitate connecting the probe cover with the medical probe while at least a portion of the probe cover remains covered by the outer wrapper. For example, a working portion of the probe and a corresponding portion of the probe cover may be retained in the outer wrapper until just prior to use.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. A protective cover set for a medical probe, comprising:
   a probe cover comprising a biocompatible, flexible polymer, the probe cover having a closed end and an open end, the probe cover being configured to receive a substantially elongate medical probe, and the probe cover being shaped for accommodating a working end of the medical probe, a handle of the medical probe, and at least a portion of a substantially elongate cord attached to the medical probe;
   an end fastening element attached at the open end of the probe cover and configured to wrap at least partially around the probe cover and around the cord of the medical probe when the medical probe is inserted in the probe cover;
   a first intermediate fastening element attached along a length of the probe cover between the closed and open ends, the first intermediate fastening element being configured to wrap at least partially around the probe cover at a first position that is adjacent to the handle of the medical probe when the medical probe is inserted in the probe cover;
   a second intermediate fastening element attached along the length of the probe cover at a second position between the first position and the open end and configured to secure the probe cover to the cord of the medical probe when the medical probe is inserted in the probe cover; and
   a removable outer wrapper enveloping at least a portion of the length of the probe cover, wherein at least the first intermediate fastening element and second intermediate fastening element are preassembled with the probe cover and contained within the outer wrapper.

2. The protective cover set of claim 1, wherein the probe cover is further shaped for accommodating a medical probe for use in an endocavity or incision.

3. A protective cover set for a medical probe, comprising:
   a probe cover comprising a biocompatible, flexible polymer, the probe cover having a closed end and an open end, and the probe cover being configured to receive a substantially elongate medical probe;
   an end fastening element attached at the open end of the probe cover and configured to wrap at least partially around the probe cover;
   a first intermediate fastening element attached along a length of the probe cover between the closed and open ends, the first intermediate fastening element being configured to wrap at least partially around a midpoint of the probe cover; and
   a removable outer wrapper enveloping at least a portion of the length of the probe cover, wherein at least the first intermediate fastening element is preassembled with the probe cover and contained within the outer wrapper.

4. The protective cover set of claim 3, further comprising:
   a second intermediate fastening element attached to the probe cover along a length of the probe cover between the first intermediate fastening element and the end fastening element.

5. The protective cover set of claim 3, wherein at least one of the end fastening element and first intermediate fastening element comprises an adhesive strip.

6. The protective cover set of claim 3, wherein at least one of the end fastening element and first intermediate fastening element comprises a non-adhesive fastener.

7. The protective cover set of claim 3, wherein the probe cover comprises one or more of thermoplastic polyurethane (TPU), thermoplastic polyethylene (TPE), and urethane.

8. The protective cover set of claim 3, wherein the probe cover comprises a first polymer layer and a second polymer layer, the first polymer layer being heat-sealed to the second polymer layer.

9. The protective cover set of claim 8, wherein the second layer comprises an at least partially transparent polyethylene, polyethylene blend, or polymer blend.

10. The protective cover set of claim 3, wherein the probe cover contains a gel.

11. The protective cover set of claim 3, wherein the probe cover has a flattened width ranging from approximately ¼ inch to approximately 4 inches, and has a length of at least 10 inches.

12. The protective cover set of claim 3, wherein the probe cover is shaped to accommodate a medical probe, a first portion of the probe cover including the closed end of the probe cover being shaped for accommodating a working end of the medical probe, and a second portion of the probe cover including the open end of the probe cover configured for accommodating a cord of the medical probe.

13. The protective cover set of claim 3, wherein the end fastening element is contained entirely within the outer wrapper prior to removal of the outer wrapper from the probe cover.

14. The protective cover set of claim 13, wherein the outer wrapper further comprises a backing and a film, the backing and film being connected to each other at a perimeter seam of the outer wrapper, the film being removable from the backing by hand.

15. The protective cover set of claim 14, wherein the outer wrapper is sized to partially envelop the probe cover, such that a portion of one of the film or the backing terminates short of the open end of the probe cover.

16. The protective cover set of claim 3, wherein the first intermediate fastening element and end fastening element are fixedly attached with the probe cover.

17. The protected cover set of claim 3, wherein the first intermediate fastening element and end fastening element are directly attached to the probe cover.

* * * * *